US011020219B2

United States Patent
Suzaki

(10) Patent No.: US 11,020,219 B2
(45) Date of Patent: *Jun. 1, 2021

(54) INTRAOCULAR LENS AND MANUFACTURING METHOD THEREOF

(71) Applicant: KOWA COMPANY, LTD., Nagoya (JP)

(72) Inventor: Asaki Suzaki, Kasugai (JP)

(73) Assignee: KOWA COMPANY, LTD., Nagoya (JP)

( * ) Notice: Subject to any disclaimer, the term of this patent is extended or adjusted under 35 U.S.C. 154(b) by 149 days.

This patent is subject to a terminal disclaimer.

(21) Appl. No.: 16/424,051

(22) Filed: May 28, 2019

(65) Prior Publication Data

US 2019/0274824 A1    Sep. 12, 2019

Related U.S. Application Data

(62) Division of application No. 15/718,675, filed on Sep. 28, 2017, now abandoned, which is a division of
(Continued)

(30) Foreign Application Priority Data

Mar. 24, 2011    (JP) ................ 2011-065836

(51) Int. Cl.
*A61F 2/16*    (2006.01)
*B29D 11/00*    (2006.01)
(Continued)

(52) U.S. Cl.
CPC .......... *A61F 2/1637* (2013.01); *B29D 11/023* (2013.01); *G02C 7/027* (2013.01); *A61F 2/1613* (2013.01); *A61F 2240/001* (2013.01)

(58) Field of Classification Search
CPC ... A61F 2/1637; A61F 2/1613; B29D 11/023; G02C 7/027
See application file for complete search history.

(56) References Cited

U.S. PATENT DOCUMENTS 6,554,425 B1    4/2003  Roffman et al.
6,609,793 B2    8/2003  Norrby et al.
(Continued)

FOREIGN PATENT DOCUMENTS

JP    2006-517676 A    7/2006
JP    2010-029694 A    2/2010
(Continued)

OTHER PUBLICATIONS

Sep. 17, 2019 Office Action issued in Indian Patent Application No. 7973/DELNP/2013.
(Continued)

*Primary Examiner* — Mathieu D Vargot
(74) *Attorney, Agent, or Firm* — Oliff PLC

(57) ABSTRACT

Provided is an intraocular lens having a novel structure with high utility which is easy to adapt to patients, and can improve quality of vision (QOV). In an intraocular lens, an optical characteristic is set rotationally symmetric around an optical axis, and a spherical aberration of a size corresponding to a coma aberration remaining in a patient's eye after extraction of a human lens of the eye is set.

2 Claims, 5 Drawing Sheets

Related U.S. Application Data application No. 14/002,831, filed as application No. PCT/JP2012/002054 on Mar. 23, 2013, now Pat. No. 9,808,340.

(51) Int. Cl.
   *B29D 11/02* (2006.01)
   *G02C 7/02* (2006.01)

(56) References Cited

U.S. PATENT DOCUMENTS

| | | | |
|---|---|---|---|
| 6,905,209 | B2 | 6/2005 | Mihashi et al. |
| 7,078,665 | B2 | 7/2006 | Topa |
| 7,697,212 | B2 | 4/2010 | Jethmalani et al. |
| 8,529,559 | B2 | 9/2013 | Liang |
| 9,808,340 | B2 * | 11/2017 | Suzaki ............ G02C 7/027 |
| 2002/0105617 | A1 | 8/2002 | Norrby et al. |
| 2006/0244916 | A1 | 11/2006 | Guillon |
| 2007/0121064 | A1 | 5/2007 | Norrby et al. |
| 2007/0268453 | A1 | 11/2007 | Hong et al. |
| 2011/0102737 | A1 | 5/2011 | Payor et al. |

FOREIGN PATENT DOCUMENTS

| | | |
|---|---|---|
| JP | 4459501 B2 | 4/2010 |
| JP | 4652558 B2 | 3/2011 |
| WO | 01/89424 A1 | 11/2001 |
| WO | 2006/088440 A1 | 8/2006 |
| WO | 2008/089999 A1 | 7/2008 |
| WO | 2009/100322 A2 | 8/2009 |
| WO | 2011/025846 A1 | 3/2011 |

OTHER PUBLICATIONS

Oct. 24, 2014 Extended Search Report issued in European Patent Application No. 12760887.5.
Aug. 28, 2015 Patent Examination Report No. 1 issued in Australian Patent Application No. 2012232611.
Oct. 29, 2015 Office Action issued in European Patent Application No. 12760887.5.
Jan. 13, 2016 Office Action issued in Japanese Patent Application No. 2013-505827.
Feb. 16, 2016 Office Action issued in Australian Patent Application No. 2012232611.
Jan. 29, 2016 Office Action issued in Russian Patent Application No. 2013147408/14(073696).
Feb. 9, 2017 European Search Report issued in European Patent Application No. 16205428.2.
Jun. 19, 2012 International Search Report issued in International Patent Application No. PCT/JP2012/002054.
Sep. 24, 2013 International Preliminary Report on Patentability issued in International Patent Application No. PCT/JP2012/002054.
Nov. 8, 2017 Office Action issued in Israeli Patent Application No. 228429.

* cited by examiner

FIG.5

| ABERRATION ($\mu m$) | | 0.00D | +0.50D | +1.00D |
|---|---|---|---|---|
| EXAMPLE 1 | $C_3^{-1}$ : 0.24 $\mu m$<br>$C_4^0$ : 0.33 $\mu m$ | | | |
| EXAMPLE 2 | $C_3^{-1}$ : 0.24 $\mu m$<br>$C_4^0$ : 0.29 $\mu m$ | | | |
| EXAMPLE 3 | $C_3^{-1}$ : 0.24 $\mu m$<br>$C_4^0$ : 0.24 $\mu m$ | | | |
| EXAMPLE 4 | $C_3^{-1}$ : 0.24 $\mu m$<br>$C_4^0$ : 0.19 $\mu m$ | | | |
| EXAMPLE 5 | $C_3^{-1}$ : 0.24 $\mu m$<br>$C_4^0$ : 0.13 $\mu m$ | | | |
| COMPARATIVE EXAMPLE 1 | $C_3^{-1}$ : 0.24 $\mu m$<br>$C_4^0$ : zero | | | |

FIG.6

| ABERRATION ($\mu$m) | | 0.00D | +0.50D | +1.00D |
|---|---|---|---|---|
| EXAMPLE 6 | $C_3^{-1}$ : 0.14$\mu$m<br>$C_4^0$ : 0.23$\mu$m | | | |
| EXAMPLE 7 | $C_3^{-1}$ : 0.14$\mu$m<br>$C_4^0$ : 0.13$\mu$m | | | |
| EXAMPLE 8 | $C_3^{-1}$ : 0.14$\mu$m<br>$C_4^0$ : 0.03$\mu$m | | | |
| COMPARATIVE EXAMPLE 2 | $C_3^{-1}$ : 0.14$\mu$m<br>$C_4^0$ : zero | | | | ary

INTRAOCULAR LENS AND MANUFACTURING METHOD THEREOF

This is a Division of application Ser. No. 15/718,675 filed Sep. 28, 2017, now abandoned, which is a Division of application Ser. No. 14/002,831 filed Oct. 4, 2013, now U.S. Pat. No. 9,808,340, which in turn is a National Stage Entry of International Application No. PCT/JP2012/002054 filed Mar. 23, 2012, which claims the benefit of Japanese Application No. 2011-065836 filed Mar. 24, 2011. The disclosure of the prior applications is hereby incorporated by reference herein in its entirety.

TECHNICAL FIELD

The present invention relates to an intraocular lens for use in the human eye, particularly an intraocular lens of a novel structure which can improve QOV (quality of vision), and the manufacturing method thereof.

BACKGROUND ART

As is well known, the human lens of the human eye may have a decrease in characteristics such as modulation ability, transparency and the like due to aging, disease or the like, and along with that, problems such as refractive error, cataracts or the like occur and visual performance decreases. As a treatment for such cases, an intraocular lens has been proposed from the past. This intraocular lens is typically inserted within the capsule in place of the human lens after the intracapsular human lens of the human eye is extracted and removed.

However, for the intraocular lens of the conventional structure, the spherical lens power is set, and an intraocular lens of a spherical lens power suited for the patient was selected and used considering the corneal curvature, ocular axis length and the like.

However, even when an intraocular lens suited for the patient is used, there were complaints such as, "It's hard to see," "I can't see objects well," and the like from patients who had the intraocular lens inserted. This kind of vision problem refers to quality of vision (QOV), and in recent years, has been found to be due to residual irregular astigmatism. Residual irregular astigmatism is due to high-order aberration of the human eye, and this cannot be corrected with conventional lenses for visual correction that correct vision using the spherical lens power and the cylindrical lens power such as intraocular lenses, glasses, or contact lenses.

To handle this kind of problem, to reduce high-order aberration in the human eye, in Japanese Patent No. 4459501 (Patent Document 1), proposed is an intraocular lens that gives wave aberration of the reverse code value to the wave aberration in the human eyes of a specified population. However, with this intraocular lens, it was difficult to say that an efficient method had been established regarding selection of the specified population, measurement of the wave aberration, setting of the reverse code value wave aberration to the intraocular lens and the like, and putting this to practical use was extremely difficult.

Specifically, as with the description noted in Patent Document 1, prescribing for the intraocular lens optical characteristics for which reverse code value high-order aberration is set so as to offset the high-order aberration of the human eye to become zero maybe ideal, but making this practical is extremely difficult. Perhaps because in addition to the fact that there are diverse high-order aberrations with the human eye, coma aberration and the like which has a particularly big adverse effect on quality of vision (QOV) has different optical characteristics around the optical axis, so the intraocular lens set with a high-order aberration for correction must be a custom made product, and not only the design but also the manufacturing of these is extremely difficult and impractical.

Though it relates to contact lenses of a different technical field than the intraocular lens that is the subject of the present invention, noted in Translated Japanese Patent application of Publication No. 2006-517676 (Patent Document 2) as a method of improving the QOV in relation to residual irregular astigmatism is the provision of a corrective lens that uses a chart for which the level of effect on the QOV is actually measured for each order of the high-order aberration expressed by Zernike polynomials, the orders of high-order aberration important for improvement of QOV is specified, and the specified high-order aberrations are offset to achieve zero. However, with this Patent Document 2, as noted in paragraphs [0097] to [0099], this is nothing more than the goal of selecting only the specified high-order aberrations that adversely affect vision, and giving a corrective lens that offsets the selected specified high-order aberrations to achieve zero. Based on examination by the inventor of the present invention, with a corrective lens power that makes only the specified high-order aberrations zero in this way, the adverse effect on vision due to other residual high-order aberration is large, and it was difficult to obtain sufficient QOV improvement effect.

In particular, with this method noted in Patent Document 2, when a corrective lens is provided with a plurality of orders of high-order aberrations as the subject, and all of those high-order aberrations are offset to reach zero, the corrective lens design and manufacturing are extremely complex and they have to be made to order, so they are not very practical, and the same kinds of problems as those of Patent Document 1 are unavoidable. Meanwhile, when providing a corrective lens that has only one high-order aberration (e.g. spherical aberration) as the subject and offsetting that to reach zero, the adverse effect due to other remaining high-order aberrations (e.g. coma aberration) is large, and it was difficult to realize good vision.

BACKGROUND ART DOCUMENTS

Patent Documents

Patent Document 1: JP-B-4459501
Patent Document 2: JP-A-2006-517676

SUMMARY OF THE INVENTION

Problem the Invention Attempts to Solve

The present invention was created with the circumstances noted above as the background, and its object is to provide an intraocular lens of a novel structure and the manufacturing method thereof that is able to effectively improve quality of vision (QOV), as well as being easy to apply to patients and having a high level of practicality.

Means for Solving the Problem

The present invention provides an intraocular lens manufacturing method including (a) an optical characteristics setting step of setting in an optical portion a spherical aberration of a size corresponding to a coma aberration remaining in a human eye of a patient from which a human lens was extracted, and of a size for which the spherical aberration remaining in that human eye of that patient will not be offset and will be made to remain; (b) a lens shape setting step of determining a lens shape of the optical portion wherein the spherical aberration set at the optical characteristics setting step is provided as a corrective optical characteristic for a residual irregular astigmatism in that human eye of that patient; and (c) a lens forming step of forming an intraocular lens having optical characteristics in which a high-order aberration of that optical portion is rotationally symmetrical around an optical axis, by means of forming the optical portion to have the lens shape determined by the lens shape setting step.

From the start, the intraocular lens of the present invention has a prerequisite of allowing coma aberration to remain in the eye of the patient, and in regards to this point, is completely different from the concept of prior art corrective lenses like that in Patent Document 1 which has the object of eliminating high-order aberration as much as possible. Then, on top of that, by actively giving spherical aberration of a size corresponding to the coma aberration to the intraocular lens, the decrease in QOV due to coma aberration is reduced.

Specifically, the present invention is focused on coma aberration among the high-order aberrations when improving vision, and in fact does not give corrective optical characteristics that offset the coma aberration, but rather is based on new knowledge of improving vision by giving spherical aberration of a size corresponding to the coma aberration as the corrective optical characteristic. In other words, it is not possible to avoid design and manufacturing being extremely difficult for improving vision as long as it is based on the prior art concept of simply achieving zero by offsetting all or specific high-order aberrations in order to suppress a decrease in vision due to high-order aberration as noted in Patent Documents 1 and 2 described previously. In contrast to this, focusing on the coma aberration which has a big adverse effect on vision, the present invention is established on a novel technical concept that is completely different from the past, which is to reduce the adverse effect due to coma aberration which is not rotationally symmetrical in relation to the optical center axis, by using spherical aberration which is rotationally symmetrical in relation to the optical center axis. In particular, with this kind of present invention, the spherical aberration given to the lens used as the corrective optical characteristic is nothing more than an optical characteristic corresponding to the coma aberration, and therefore it goes without saying that it does not achieve zero by offsetting the coma aberration, and it does not achieve zero by offsetting spherical aberration, either. It should be understood that this is technology of a completely different perspective from that of the past, which makes having coma aberration and spherical aberration remain be something affirmative.

In fact, by setting spherical aberration in the intraocular lens, being able to effectively deal with coma aberration which has a large adverse effect on QOV has a large significance when manufacturing or handling intraocular lenses, when doing surgery or the like, which are implementations of the present invention. Specifically, with a focus only on coma aberration, to give wave aberration of the reverse code to the coma aberration, a complex lens surface shape that is rotationally asymmetrical must be given to the intraocular lens, and not only is the design and manufacturing thereof extremely difficult, but when inserting into the eye as well, it is necessary to have precise alignment in the circumference direction, so this is not practical. In contrast to this, the intraocular lens for which spherical aberration is set according to the present invention is formed having optical characteristics that are rotationally symmetrical around the optical axis, so it is not necessary to specify a position in the circumference direction such as during the manufacturing process or when inserting in the eye, so manufacturing and handling are easy, which makes it easy to put this to practical use.

In other words, in addition to finding that it is possible to reduce the decrease in QOV due to coma aberration by using spherical aberration, focus was placed on being able to perform setting of spherical aberration in the intraocular lens with the intraocular lens optical characteristics left being rotationally symmetrical, and the present invention was completed by combining these with each other. Then, if the present invention which was completed based on this kind of novel basic concept is followed, it became possible to provide a novel intraocular lens which can reduce the decrease in QOV due to coma aberration which is one type of high-order aberration for which a practical countermeasure was extremely difficult in the past, and to give good QOV, while being sufficiently practical in terms of manufacturing and implementation.

With the present invention, to deal with the decrease in QOV due to coma aberration remaining in the human eye from which the human lens was extracted, the fact that it is effective to actively give spherical aberration using the intraocular lens has been objectively confirmed by comparison between examples and comparative examples in the embodiment described later. When examined by the inventor of the present invention, at least the subjective focal depth is made deeper by giving spherical aberration, and it is thought that this is an item for which one technical basis is acknowledged. In particular, the QOV improvement effect exhibited by the intraocular lens according to the present invention is also clear from the example data described later.

However, the spherical aberration with the intraocular lens of the present invention is set at a size corresponding to the coma aberration, and if the coma aberration is large, then large spherical aberration is set, and if the coma aberration is small, then small spherical aberration is set. Here, the specific correlation of the setting value of the spherical aberration of the intraocular lens in relation to the coma aberration remaining in the eye of the patient can be determined considering not only objective optical characteristics of the patient's eye, but also subjective vision preferences of the patient or the like.

For this kind of determination method, a device that can easily measure the spherical aberration for not only the lens optical system but also the human eye optical system is disclosed in Japanese Patent No. 4652558, the specification of U.S. Pat. No. 7,078,665 and the like, and for example since the OPAL 300 (product name) made by Spot Optics Corp. is available on the market as a wave aberration measurement device using the Shack-Hartmann Method, a person skilled in the art could implement this easily. In particular, when determining the value of the spherical aberration corresponding to the coma aberration with the eye optical system, it is not necessary to match both items, as described above. For example, even when dealing with contact lenses or glasses, prescription is ultimately left to the subjective vision sense of the user, or is selected based on consideration of the application. From this point of view, determination of the value of the spherical aberration should be handled by the person skilled in the art by referencing the user's opinion, the eye optical system objective measurement information or the like. Thus, compared to the prior art structure contact lenses as noted in Patent Documents 1 and 2, for example, implementing the present invention does not involve an impractical level of difficulty. Of course, with the present invention, to make it possible to more easily and quickly determine the spherical aberration, it is effective to further narrow the selection range of the spherical aberration, and from that objective, it is preferable to use the optical characteristics selection technology given by the formulas and the like noted hereafter.

Specifically, with the human eye, even in a state with the human lens extracted, there are cases when there is spherical aberration due to the shape of the cornea and the like, for example. In that case, the spherical aberration set for the intraocular lens of the present invention is designed considering the spherical aberration remaining in the human eye with the human lens extracted. In specific terms, at the optical characteristics setting step, the spherical aberration of the optical portion with the intraocular lens (RMS value) is preferably set with an RMS value that satisfies any of the following formulas in relation to the coma aberration remaining in the eye after the human lens is extracted (RMS value).

Intraocular lens spherical aberration≥Coma aberration remaining in the eye after lens extraction−0.37 μm Intraocular lens spherical aberration≤Coma aberration remaining in the eye after lens extraction−0.17 μm The RMS value is the value (unit: μm) for which the wave aberration in the pupil area of the human eye optical system is put into numerical form (displayed as root mean square) using a wave aberration analysis device (wave sensor). According to the formulas noted above, by giving spherical aberration corresponding to the coma aberration of the patient eye to the intraocular lens, it is easy to obtain good QOV that also considers the spherical aberration remaining in the cornea.

Also, the optical characteristics of the human eye tend to change as age increases. In light of that, using the optical characteristics of the cornea or the like, for example, it is possible to estimate the coma aberration remaining in the patient after the human lens is extracted according to the age of the patient. From this perspective, as a result of additional examination by the inventor of the present invention, with the optical characteristics setting step, setting the spherical aberration set for the optical portion in the intraocular lens (RMS value) using the patient age corresponding to the coma aberration as an index based on the following formulas is also effective for obtaining good QOV.

Intraocular lens spherical aberration=$A+B$×Patient age $-0.4 \leq A$ (μm)$\leq -0.1$
$0.003 \leq B$ (μm)$\leq 0.004$ Furthermore, considering the fact that coma aberration, which is one human eye optical characteristic, changes according to age, additional examination was made by the inventor of the present invention. As a result, it was found that from human eye optical characteristics measurement data for the population of the same age bracket as the patient for which the human lens has been extracted, it is possible to find an intraocular lens spherical aberration that will give good QOV to that patient. Specifically, with the optical characteristics setting step, using an intraocular lens for which the spherical aberration for the optical portion is set using the difference between the average value of the measurement data of the human eye spherical aberration for the same age bracket population as the patient and the spherical aberration of the cornea of that patient is effective for obtaining good QOV.

Also, the present invention provides an intraocular lens for which the spherical aberration of a size corresponding to the coma aberration remaining in the human eye of a patient from which the human lens has been extracted, and of a size for which the spherical aberration will not be offset and will be made to remain in the human eye of that patient is set for the optical portion as the corrective optical characteristic for residual irregular astigmatism in the human eye of that patient, and for which the high-order aberration for the optical portion is rotationally symmetrical around the optical axis.

As is clear from the description above, the intraocular lens with this kind of structure can give good QOV to patients, and in fact the design and manufacturing can be realized easily, so it is easy to provide on the market and put to practical use. The intraocular lens of this kind of structure according to the present invention is preferably manufactured using the method of the present invention described above. Also, each preferred mode noted in the description of the manufacturing method above can be applied to the intraocular lens of the present invention as long as it is structurally feasible.

Also, with the intraocular lens of the present invention, it is preferable that at least one of the spherical aberration value set according to the method of the present invention as described above or the RMS value is displayed on at least one of the lens main unit, its individual package, the housing package or the housing box.

Effect of the Invention

If the present invention is followed, the QOV is improved by applying spherical aberration, which is an optical characteristic that is rotationally symmetrical around the optical axis, in relation to coma aberration having a big adverse effect on QOV and for which it is difficult to realize an intraocular lens having optical characteristics that offset the coma aberration. Accordingly, it is possible to realize an intraocular lens of a novel structure for which design, manufacturing, and handling are easy, and practical usability is excellent.

BRIEF DESCRIPTION OF THE DRAWINGS

FIG. 5 is a simulation optical image showing the vision during application to the human eye of the same patient for the intraocular lens as the first through fifth examples of the present invention as well as for a comparative example 1 for which spherical aberration was set to zero.

FIG. 6 is a simulation optical image showing the vision during application to the human eye of the same patient for the intraocular lens as the sixth through eighth examples of the present invention as well as for a comparative example 2 for which spherical aberration was set to zero.

EMBODIMENTS FOR CARRYING OUT THE INVENTION

Figure 1:
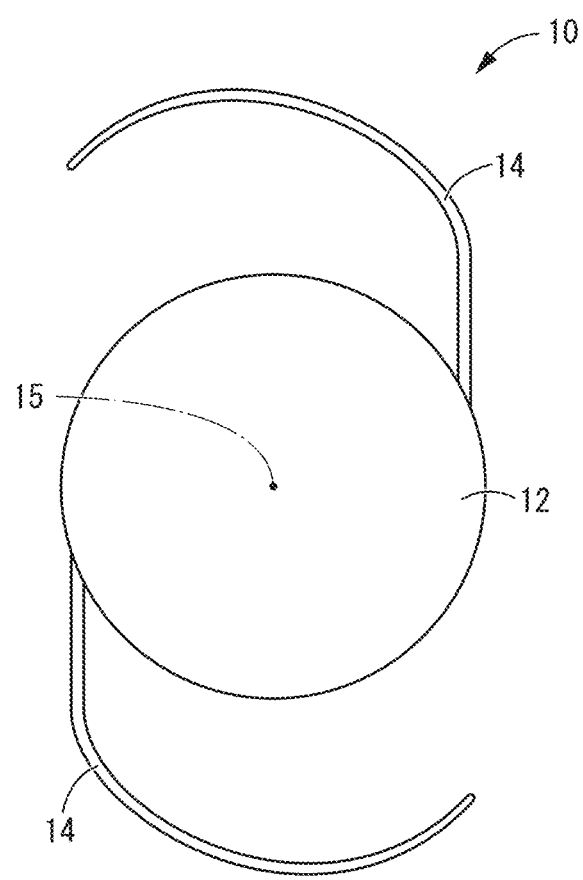
FIG. 1 is a front view showing an intraocular lens as one embodiment of the present invention.

Following, we will describe an embodiment of the present invention while referring to the drawings. First, in FIG. 1, an intraocular lens 10 is shown as an embodiment of the present invention.

This intraocular lens 10 is constituted including an optical portion 12 that gives optical characteristics constituting the lens main unit, and a pair of support units 14, 14 extending out from the optical portion 12. The optical portion 12 is equipped with a front surface and back surface for which respectively roughly spherical convex surface shapes are the lens surfaces, these front and back surfaces are refractive surfaces, and designated optical characteristics are set. With this embodiment, the geometric center axis of the optical portion 12 and the optical axis (optical center axis) are set to be the same, and this is used as a lens center axis 15. Meanwhile, the pair of support units 14, 14 are formed extending out facing the direction mutually opposite from two locations positioned facing mutually opposite in the radial direction of the outer circumference edge part on the optical portion 12. Also, the tip part of each support unit 14 is a free edge that extends curving in the circumference direction of the optical portion 12.

Figure 2:
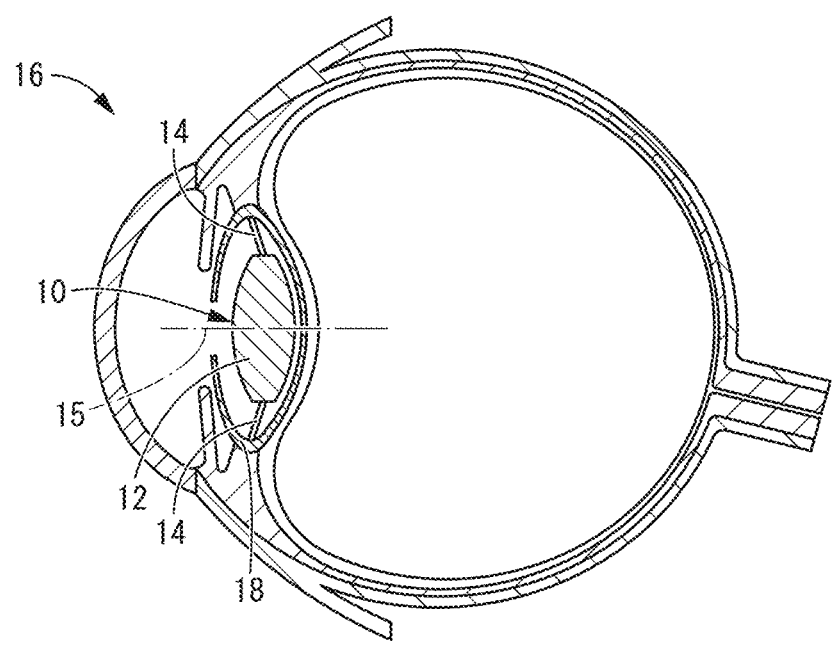
FIG. 2 is a vertical cross section explanatory view of a human eye in which the intraocular lens shown in FIG. 1 is inserted.

Then, as shown in FIG. 2, this intraocular lens 10 is installed in place of the human lens by being inserted inside a human lens capsule 18 after removal of the human lens for a human eye 16 of the patient. Under these circumstances, the tip part of the support units 14, 14 abut the circumference edge part of the human lens capsule 18, and the optical portion 12 is held in a designated position of the center inside the human lens capsule 18.

The material of the intraocular lens 10 is not limited by the present invention, and it is possible to use polymethyl methacrylate (PMMA), silicone rubber or the like known from the past as the material of the optical portion 12. It is also possible to use known various synthetic resin materials for the support units 14, 14 as well, but it is also possible to have a one piece structure with the optical portion 12 and the support units 14, 14 formed as an integrated unit.

However, with the intraocular lens 10 of this embodiment, spherical aberration is actively given to the optical portion 12. Specifically, as the original function of the intraocular lens, the intraocular lens 10 of the present invention has as the optical characteristics spherical aberration in addition to the spherical lens power (D) that replaces the human lens.

As is well known, the value of the spherical lens power (D) is determined based on the ocular axis length and corneal shape of the patient, and typically a value of approximately +10 to 25 D is set. In most cases, the spherical lens power is set as a single focal point, but it is also acceptable to have multiple focal points set.

Meanwhile, the spherical aberration for the optical portion 12 of the intraocular lens 10 is set at a size corresponding to the value of the coma aberration remaining in the human eye 16 of the patient for which the human lens was extracted, and of a size such that the spherical aberration will not be offset and will be made to remain in the human eye 16 of the patient. In specific terms, with the human eye 16 of the patient for which the intraocular lens has been inserted, the spherical aberration is set for the optical portion 12 of the intraocular lens so that the size of the coma aberration is roughly the same level as the spherical aberration. In this way, the manufacturing method of the intraocular lens 10 with this embodiment is constituted including the optical characteristics setting step. The coma aberration and the spherical aberration values can both be represented by RMS values (μm). In other words, the volume of skew in the light ray direction by the actual wave surface in relation to the virtual wave surface orthogonal to the light rays expresses each aberration as a value expressed in root mean square on that virtual wave surface. Also, the coma aberration existing in the human eye 16 of the patient in which the intraocular lens 10 is inserted is almost all according to the cornea with the present invention using the intraocular lens 10 having optical characteristics rotationally symmetrical around the optical axis. The coma aberration of the cornea of the patient can be found based on cornea topography measurement values obtained using, for example, a keratometer, a reflex keratometer, or a wave surface sensor. For example, the $C_3^1$ and $C_3^{-1}$ terms are the horizontal coma aberration and vertical coma aberration with Zernike polynomials obtained by performing wave aberration analysis, for example, and the coma aberration is expressed as a synthetic vector volume of the horizontal coma aberration and the vertical coma aberration.

At that time, spherical aberration by an ocular tissue other than the intraocular lens 10 exists in the human eye 16 in which the intraocular lens has been inserted. Almost all the spherical aberration remaining in the human eye 16 after the human lens is extracted is due to the cornea. Because of that, the spherical aberration of the intraocular lens 10 itself is determined considering the spherical aberration of the cornea of the patient. The spherical aberration of the cornea of the patient can be found based on measurement values by the same kind of measurement devices as the coma aberration noted above. For example, the $C_4^0$ term with a Zernike polynomial obtained by performing wave aberration analysis is used as the spherical aberration. Therefore, the spherical aberration value set for the intraocular lens 10 can be found based on the formula below.

> Intraocular lens spherical aberration="Coma aberration remaining in the eye after lens extraction"−"Cornea spherical aberration"

However, with the formula above, "Intraocular lens spherical aberration" is not necessarily optimally perfectly matched to the right side of the equation ("coma aberration remaining in the eye after lens extraction"−"cornea spherical aberration"). Perhaps this is because the vision (QOV) is a subjective item and there is a big individual difference, and for example the intraocular lens spherical aberration judged to be optimum may be different between a patient who senses that having a big difference in sharpness due to a difference in the distance from the subject item is not desirable, and a patient who thinks he'd like to observe only objects of a specified distance at the highest level of sharpness.

Figure 3:
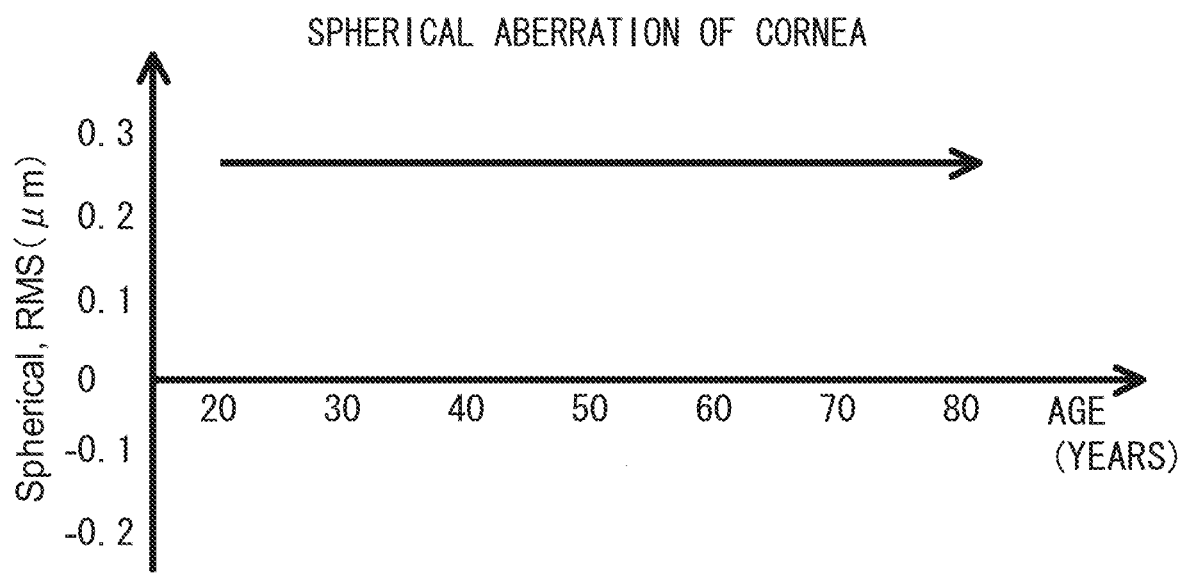
FIG. 3 is a graph for explaining the change with aging of the spherical aberration of the cornea in the human eye.

Also, as shown in FIG. 3, the corneal spherical aberration of the human eye 16 almost doesn't change at all with aging, and it is possible to estimate the average spherical aberration across all ages to be 0.27 μm (RMS). Considering this fact, it is possible to use the following formulas to express the preferable setting range of the spherical aberration (RMS value) for the optical portion 12 of the intraocular lens 10 set with the optical characteristics setting process described previously.

Figure 4:
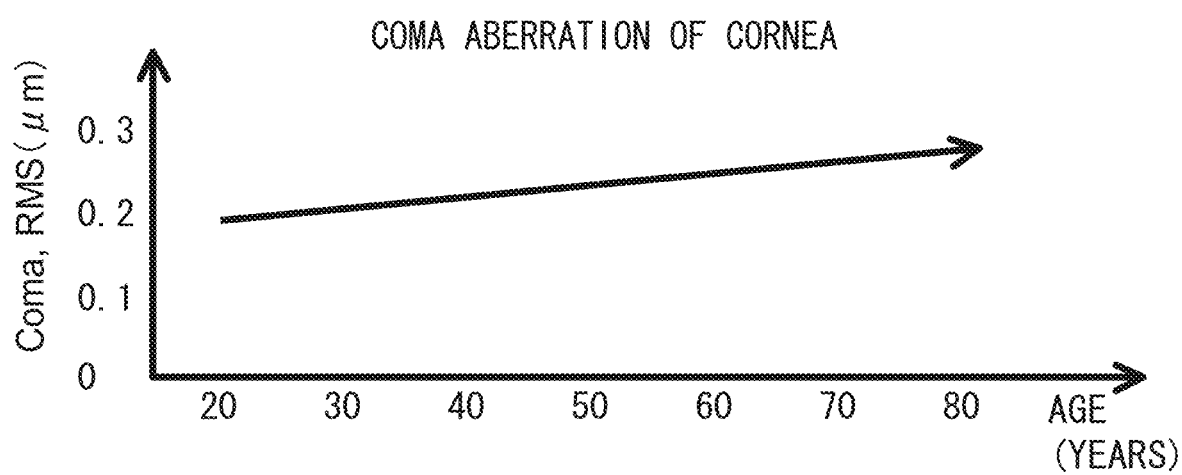
FIG. 4 is a graph for explaining the change with aging of the coma aberration of the cornea in the human eye.

> Intraocular lens spherical aberration≥Coma aberration remaining in the eye after lens extraction− 0.37 μm > Intraocular lens spherical aberration≤Coma aberration remaining in the eye after lens extraction− 0.17 μm Furthermore, the coma aberration remaining in the eye after lens extraction is almost all due to the cornea, and as shown in FIG. 4, that cornea coma aberration changes as a linear function according to aging in a range of roughly 0.2 to 0.3 µm. Considering this fact, the preferable setting range of the spherical aberration (RMS value) with the optical portion 12 of the intraocular lens 10 set during the optical characteristics setting process described previously can be expressed using the following formulas for which A and B are each constants.

Intraocular lens spherical aberration=$A+B\times$Patient age $-0.4 \leq A$ (µm) $\leq -0.1$ $0.003 \leq B$ (µm) $\leq 0.004$ Also, with a different approach considering that the human eye optical characteristics change with aging, it is also preferable to set the spherical aberration value for the optical portion 12 of the intraocular lens 10 set during the optical characteristics setting process described previously within a specific range determined based on the human eye optical characteristics of the population when a plurality of healthy persons in the same age level as the patient is set as the population.

In specific terms, the difference between the average value of the spherical aberration measurement data of the human eye (entire eye optical system including the cornea and the human lens) with the population noted above and the spherical aberration of the cornea of the patient is set as the spherical aberration of the intraocular lens 10 used for that patient. The fact that the intraocular lens 10 spherical aberration set in this way is roughly equal to the spherical aberration that the human lens has in the human eye of a healthy person which is the population noted above was discovered by the inventor of the present invention.

As described above, in the preferred setting range, the spherical aberration determined considering the coma aberration and the spherical aberration remaining in the human eye 16 of the patient for which the human lens was extracted, specifically, the spherical aberration having the corrective optical characteristics for residual irregular astigmatism set with the optical characteristics setting process described previously and the spherical lens power corresponding to the spherical power remaining in the human eye 16 of the patient for which the human lens was extracted are both set as optical characteristics that are rotationally symmetrical around the optical axis, and by doing this, the lens shape setting process that determines the target optical characteristics (lens shape) of the intraocular lens 10 is performed. As is well known by a person skilled in the art involved in the design of optical lenses, if the setting values of the optical characteristics are determined in this way, the specific shape of the intraocular lens 10 (shape of the refractive surface) can be set using various types of well known lens design software using a ray tracing algorithm based on Snell's Law, for example. The shape of this intraocular lens 10 is specified by a multi-linear function or the like as the radial direction cross section shape of the lens front and back, for example. After that, the optical portion 12 of the lens shape based on the design information determined with the lens shape setting process described previously is formed by a lens forming process using a specific lens material and using a well known molding method, lathe turning method or the like, and the intraocular lens 10 having the target optical characteristics is manufactured.

Then, the intraocular lens 10 for which the shape was determined in this way is roughly in a disk shape, and is equipped with rotationally symmetrical optical characteristics with the lens center axis 15 as the rotational center axis. Also, with the optical portion 12 of the intraocular lens 10, the high-order aberration is rotationally symmetrical around the lens center axis 15, and since asymmetrical optical characteristics are not set in the circumference direction around the lens center axis 15 such as coma aberration or the like, in typical cases when a prerequisite is using a uniform lens material, the lens front and back shape is also a rotating body shape with the lens center axis 15 as the rotation center axis. By doing this, with the intraocular lens 10, at any stage, including manufacturing, handling, insertion into the human eye 16 or the like, it is possible to easily perform design and manufacturing as well as do surgery without specially considering alignment in the circumference direction.

Incidentally, as described above, a number of the simulation results performed to confirm that good QOV was given by the intraocular lens 10 with this embodiment are shown hereafter as examples of the present invention.

First, FIG. 5 shows the simulation results when the intraocular lens manufactured according to the present invention was used for a 60 year old patient. With this simulation, using optical design software ZEMAX (product name, made by Zemax Development Corp. of the U.S.), as an eyeball model of a 60 year old patient, an item with coma aberration (vertical coma aberration volume of the $C_3^{-1}$ term with a Zernike polynomial) of 0.24 µm was constructed, and optical characteristics of the eye optical system correlating to the optical area applicable to a pupil of 6 mm were evaluated with a Landolt ring simulation optical image. Specifically, examples 1 through 5 and comparative example 1 all correlate to a human eye in which the intraocular lens is inserted, and are thought to be items for which coma aberration of 0.24 µm remains. Then, for each model of these examples 1 through 5 and comparative example 1, with the point for which the focal point position by spherical lens power is optimum (0.00 D) as a reference, a simulation optical image of each position when the focal point position is skewed in the near direction by a distance correlating to 0.50 D and 1.00 D from there was obtained, and the vision (QOV) was assessed using those.

For that human eye, with comparative example 1, according to the technical concept as noted in Patent Document 1, for example, this correlates to a case when the intraocular lens was inserted so as to have the spherical aberration (spherical aberration volume of the $C_4^0$ term with a Zernike polynomial) become zero (namely, for which spherical aberration of the reverse code was set so as to offset the spherical aberration remaining in the cornea). Meanwhile, with examples 1 through 5, in all cases, this correlates to a case when the intraocular lens was inserted with optical characteristics for which spherical aberration was set actively according to the present invention. In particular, the example 3 correlates to a case when the spherical aberration of the intraocular lens was set considering the spherical aberration of the cornea so that spherical aberration of the same RMS value as the coma aberration remaining in the human eye is set.

From the results of the simulation optical image shown in FIG. 5, it is clear that compared to a case when the spherical aberration is offset and set to zero, the case of actively setting spherical aberration in the human eye suppresses changes in vision (image quality) that come with changes in the focal point position. Specifically, with comparative example 1, with the optimum focal point position (0.00 D), the image clarity is high, but as that is moved away from, there is a sudden drop in vision, and at a position changed by 1.00 D, it is almost impossible to see, and it is only possible to see items of a specified distance, so we can understand that ensuring quality of vision is difficult. Also, not only with example 3 for which the spherical aberration was set optimally, but particularly with the items of examples 2 and 4, even at a position changed by 1.00 D, it is clear that the quality of the image is ensured well compared to comparative example 1.

Also, FIG. 6 shows the simulation results when using an intraocular lens manufactured according to the present invention for a 20 year old patient. With this simulation, the same as with examples 1 through 5 noted above, using ZEMAX, as the eyeball model of a 20 year old patient, an item of coma aberration (vertical coma aberration volume of the $C_3^{-1}$ term with the Zernike polynomial) of 0.14 μm was constructed, and for optical characteristics of the eye optical system correlating to the optical area corresponding to a pupil of 6 mm, a Landolt ring simulation optical image was obtained and vision was assessed.

Specifically, the same as with comparative example 1, comparative example 2 correlates to a case of offsetting the cornea spherical aberration with the intraocular lens spherical aberration and having the spherical aberration of the eye optical system be zero. Meanwhile, with examples 6 through 8, all of these correlate to cases for which an intraocular lens was inserted with optical characteristics for which spherical aberration of the eye optical system was set actively according to the present invention. In particular, example 7 is an item for which spherical aberration of roughly the same RMS value as the coma aberration of the eye optical system was set.

From the results of the simulation optical image shown in FIG. 6, as shown in examples 6 through 8, compared to a case when the spherical aberration is offset and set to zero, a case when spherical aberration corresponding to the remaining coma aberration is actively set can be understood to be advantageous in ensuring overall quality of vision by being able to suppress changes in vision (image quality) that come with changes in the focal point position.

KEYS TO SYMBOLS

10: Intraocular lens
12: Optical portion
16: Human eye

The invention claimed is:

1. An intraocular lens manufacturing method comprising:
an optical characteristics setting step of setting in an optical portion of the intraocular lens a spherical aberration of an amount for which a spherical aberration and a coma aberration remaining in a human eye of a patient from which a human lens was extracted will not be offset;
a lens shape setting step of determining a lens shape of the optical portion wherein the spherical aberration set at the optical characteristics setting step is provided as a corrective optical characteristic for a residual irregular astigmatism in that human eye of that patient; and
a lens forming step of forming an intraocular lens having optical characteristics in which a high-order aberration of that optical portion is rotationally symmetrical around an optical axis, by means of forming the optical portion to have the lens shape determined by the lens shape setting step,
wherein at the optical characteristics setting step, the spherical aberration set for the optical portion is set with an RMS value that satisfies all of the following formulas, where A and B are constants:

Intraocular lens spherical aberration=$A+(B\times\text{Patient age, in years})$;

$-0.4 \leq A$ (μm) $\leq -0.1$; and
$0.003 \leq B$ (μm) $\leq 0.004$.

2. An intraocular lens manufacturing method comprising:
an optical characteristics setting step of setting in an optical portion of the intraocular lens a spherical aberration of an amount for which a spherical aberration and a coma aberration remaining in a human eye of a patient from which a human lens was extracted will not be offset;
a lens shape setting step of determining a lens shape of the optical portion wherein the spherical aberration set at the optical characteristics setting step is provided as a corrective optical characteristic for a residual irregular astigmatism in that human eye of that patient; and
a lens forming step of forming an intraocular lens having optical characteristics in which a high-order aberration of that optical portion is rotationally symmetrical around an optical axis, by means of forming the optical portion to have the lens shape determined by the lens shape setting step,
wherein at the optical characteristics setting step, the spherical aberration set for the optical portion is set by using a difference between an average value of measurement data of human eye spherical aberrations of a population of a same-age bracket with the patient and the spherical aberration of a cornea of the patient.

* * * * *